(12) United States Patent
Oh et al.

(10) Patent No.: US 10,702,575 B2
(45) Date of Patent: Jul. 7, 2020

(54) PHARMACEUTICAL COMPOSITION FOR PREVENTING OR TREATING MYCOBACTERIUM SPECIES INFECTION AND METHOD USING THE SAME

(71) Applicant: Seoul National University R&DB Foundation, Seoul (KR)

(72) Inventors: Dong Chan Oh, Seoul (KR); Yern Hyerk Shin, Seoul (KR); Eun Kyeong Jo, Daejeon (KR); Hye Mi Lee, Daejeon (KR); Tae Sung Kim, Daejeon (KR); Won Kim, Seoul (KR)

(73) Assignee: Seoul National University R&DB Foundation, Seoul (KR)

( * ) Notice: Subject to any disclaimer, the term of this patent is extended or adjusted under 35 U.S.C. 154(b) by 79 days.

(21) Appl. No.: 15/887,862

(22) Filed: Feb. 2, 2018

(65) Prior Publication Data
US 2018/0221437 A1    Aug. 9, 2018

(30) Foreign Application Priority Data
Feb. 2, 2017 (KR) ........................ 10-2017-0015124

(51) Int. Cl.
*A61K 38/12* (2006.01)
*A61P 31/06* (2006.01)
*A61K 45/06* (2006.01)

(52) U.S. Cl.
CPC .............. *A61K 38/12* (2013.01); *A61P 31/06* (2018.01); *A61K 45/06* (2013.01)

(58) Field of Classification Search
CPC .......... A61K 38/12; A61K 45/06; A61P 31/06
See application file for complete search history.

(56) References Cited

U.S. PATENT DOCUMENTS

| 9,090,667 B2 | 7/2015 | Kim et al. | |
| 2014/0142031 A1* | 5/2014 | Kim ........................ | C07K 7/54 514/2.9 |

FOREIGN PATENT DOCUMENTS

| KR | 10-2014-0114522 A | 9/2014 |
| KR | 10-1522625 | 5/2015 |
| KR | 10-2015-0144812 | 12/2015 |
| WO | WO 2012/144790 A | 10/2012 |

OTHER PUBLICATIONS

Gao et al, Antimicrobial Agents and Chemotherapy, Feb. 2015, vol. 39, No. 2, 880-889 (Year: 2015).*
Um et al., J.Org.Chem., 2013, 78, 12321-12329) (Year: 2013).*
Dionne, et al., "*Drosophila melanogaster* is a Genetically Tractable Model Host for Mycobacterium Marinum," *Infection and Immunity*, Jun. 2003, pp. 3540-3550.
Stehr, et al., "Filling the Pipeline—New Drugs for an Old Disease," *Current Topics for Medicinal Chemistry*, 2014, 14, pp. 110-129.
Tae Sung Kim et al., "Ohmyungsamycms, New Antimycobacterial Cyclic Peptides, Activate Autophagy via AMP-activated Protein Kinase-mediated Signaling," *MSK2016 International Meeting of the Microbiological Society of Korea*, Apr. 2016.
Tae Sung Kim et al, "Olmyungsamycins Promote Antimicrobial Responses Through Autophagy Activation via AMP-activated Protein Kinase Pathway and Reactive Oxygen Species Generation," *KM2016 43rd Annual Meeting & International Symposium*, Jun. 2016.
Tae Sung Kim et al., "Antimycobacterial Cyclic Peptides, Ohmyungsamycins, Inhibit Macrophage Inflammatory Responses Induced by Mycobacterial Infection through Activation of AMP-activated Protein Kinase Pathway," *The 24th Federation Meeting of Korean Basic Medical Scientists*, 2016.
Tae Sung Kim et al, "Ohmyungsamycins activate autophagy through AMP-activated protein kinase and reactive oxygen species generation during mycobacterial infection" *2016 International Conference of the Korean Socity for Molecular and Cellular Biology*, Oct. 2016.
Korean Intellectual Property Office, Notice of Final Rejection, dated Oct. 15, 2018, in Republic of Korea Application No. 10-2017-0015124.
Itakura, Iisuke et al., "Characterization of autophagosome formation site by a hierarchical analysis of mammalian Agt proteins," *Autophagy*, 6(6):764-776 (Aug. 2010).

* cited by examiner

*Primary Examiner* — Sudhakar Katakam
(74) *Attorney, Agent, or Firm* — Klarquist Sparkman, LLP

(57) ABSTRACT

Provided are a pharmaceutical composition for preventing or treating *Mycobacterium* sp. infection or a related symptom thereof, wherein the pharmaceutical composition includes a compound including a peptide represented by Formula 1, or an isomer, a derivative, a solvate, or a pharmaceutically acceptable salt thereof; and a method using the same. The pharmaceutical composition has anti-*Mycobacterium tuberculosis* activity against Mycobacteria, e.g., *Mycobacterium tuberculosis*, and palliates inflammatory response caused by *Mycobacterium tuberculosis*. Thus, the pharmaceutical composition may be used in preventing or treating *Mycobacterium* sp. infection or a related symptom thereof.

9 Claims, 12 Drawing Sheets

PHARMACEUTICAL COMPOSITION FOR PREVENTING OR TREATING MYCOBACTERIUM SPECIES INFECTION AND METHOD USING THE SAME

CROSS-REFERENCE TO RELATED APPLICATION

This application claims the benefit of Korean Patent Application No. 10-2017-0015124, filed on Feb. 2, 2017, in the Korean Intellectual Property Office, the disclosure of which is incorporated herein in its entirety by reference.

BACKGROUND

1. Field

One or more embodiments relate to a pharmaceutical composition including a cyclic peptide compound for preventing or treating *Mycobacterium* sp. infection and a method of using the pharmaceutical composition.

2. Description of the Related Art

Tuberculosis is an infectious disease that has existed even back in approximately 7,000 BC in Stone Age. Although tuberculosis is an old disease, tuberculosis still accounts for a considerable number of deaths of young people all over the world. *Mycobacterium tuberculosis* causing tuberculosis became known in 1882 by German bacteriologist Robert Koch. Infection with *Mycobacterium tuberculosis* does not necessarily cause tuberculosis. *Mycobacterium tuberculosis* is latent in a body of the subject, and then tuberculosis occurs when the subject has a low level of immunity. It is estimated that about 30% of the world's population is infected with *Mycobacterium tuberculosis*. Even though a proliferation rate of *Mycobacterium tuberculosis* is slower than that of common infectious bacteria, *Mycobacterium tuberculosis* is characterized by its ability to survive in the macrophage while causing a mutation to have resistance to various drugs. Therefore, as a treatment method of tuberculosis, it is difficult for a general single drug prescription to have therapeutic effect. Thus, it is recommended to treat for a long time with a combination of various medicines.

Various compounds such as isoniazid (INH), rifampicin, ethambutol (EMB), pyrazineamide, streptomycin, and kanamycin have been used as antituberculosis drugs. However, INH may cause peripheral neuritis, rifampicin may cause thrombocytopenia, streptomycin may cause equilibrium or hearing loss, or peripheral neuropathy, EMB may cause visual impairment, and pyrazinamide may cause hyperuricemia. Thus, there is a problem that the types of antituberculosis drugs are not diverse, and the number of prescriptions or capacity is limited due to various side effects of each drug. In addition, a compound having antituberculosis activity is under development (Korean Patent Application Pub. No. 10-2015-0144812 (published on Dec. 28, 2015)).

Therefore, it is necessary to select a new antituberculosis drug having antituberculosis activity and fewer side effects.

SUMMARY

Provided is a pharmaceutical composition for preventing or treating *Mycobacterium* sp. infection or a related symptom thereof, the pharmaceutical composition including: a cyclic peptide compound, or an isomer, a derivative, a solvate, or a pharmaceutically acceptable salt thereof.

Provided is a method of preventing or treating *Mycobacterium* sp. infection or a related symptom thereof, using a cyclic peptide compound, or an isomer, a derivative, a solvate, or a pharmaceutically acceptable salt thereof.

Additional aspects will be set forth in part in the description which follows and, in part, will be apparent from the description, or may be learned by practice of the presented embodiments.

According to an aspect of the present disclosure, a pharmaceutical composition for preventing or treating *Mycobacterium* sp. infection or a related symptom thereof includes: a compound including a peptide represented by Formula 1, or an isomer, a derivative, a solvate, or a pharmaceutically acceptable salt thereof.

According to another aspect of the present disclosure, a method of preventing or treating *Mycobacterium* sp. infection or a related symptom thereof, using the compound, or an isomer, a derivative, a solvate, or a pharmaceutically acceptable salt thereof.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1A:
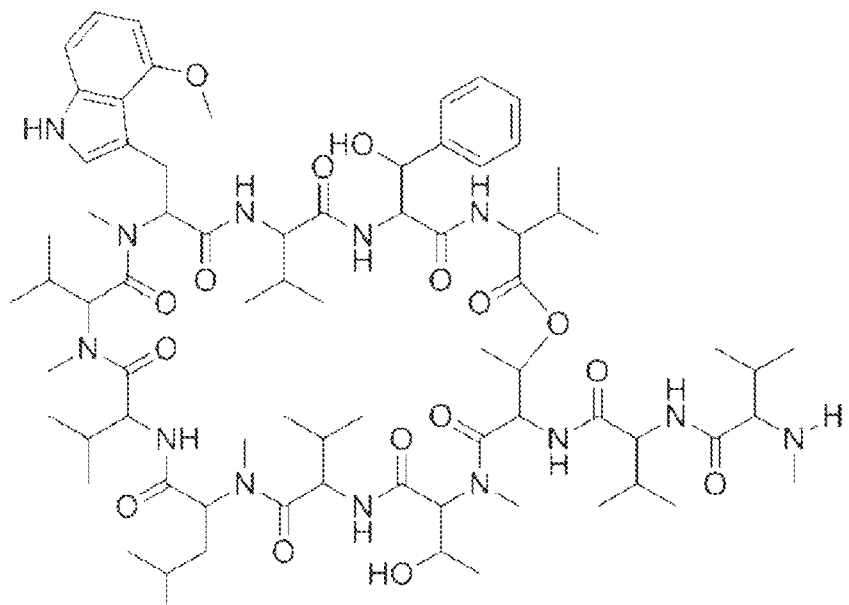
FIG. 1A illustrates a formula of Ohmyungsamycin A (OMS-A)
Figure 1B:
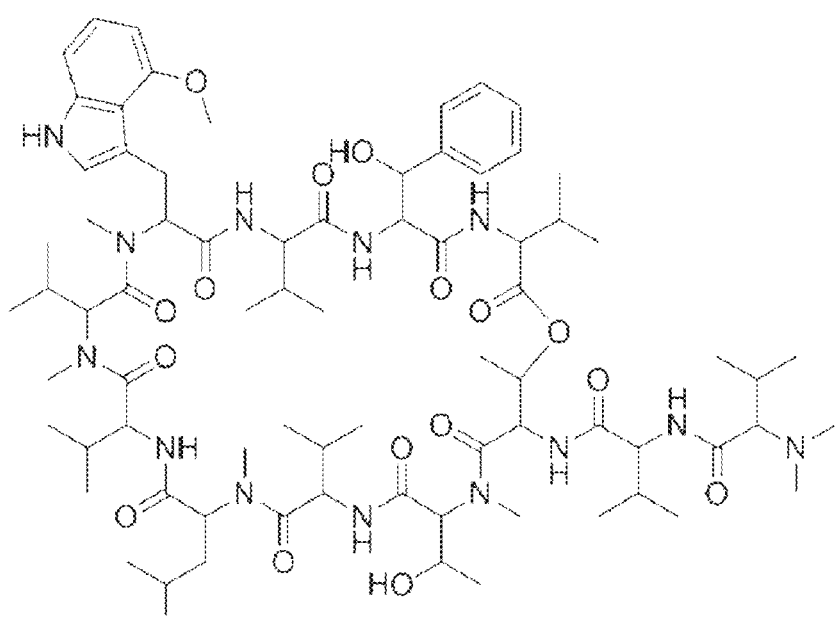
FIG. 1B illustrates a formula of Ohmyungsamycin B (OMS-B)

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items.

An aspect of the present disclosure provides a pharmaceutical composition for preventing or treating *Mycobacterium* sp. infection or a related symptom thereof, the pharmaceutical composition including: a compound including a peptide represented by Formula 1, or an isomer, a derivative, a solvate, or a pharmaceutically acceptable salt thereof:

Formula 1

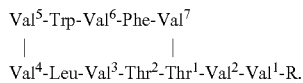

Val⁴-Leu-Val³-Thr²-Thr¹-Val²-Val¹-R.

In Formula 1, Val, Thr, Leu, Trp, and Phe respectively represent valine, threonine, leucine, tryptophan, and phenylalanine.

In Formula 1, R may be H, a substituted or unsubstituted $C_1$-$C_{20}$ alkyl group, a substituted or unsubstituted $C_2$-$C_{20}$ alkenyl group, a substituted or unsubstituted $C_2$-$C_{20}$ alkynyl group, a substituted or unsubstituted $C_3$-$C_{20}$ aryl group, or a combination thereof. Examples of the $C_1$-$C_{20}$ alkyl group include a $C_1$-$C_{15}$ alkyl group, a $C_1$-$C_{10}$ alkyl group, a $C_1$-$C_5$ alkyl group, and a $C_1$-$C_3$ alkyl group. Examples of the $C_1$-$C_{20}$ alkyl group include a methyl group. Examples of the $C_2$-$C_{20}$ alkenyl group include a $C_2$-$C_{15}$ alkenyl group, a $C_2$-$C_{10}$ alkenyl group, and a $C_2$-$C_5$ alkenyl group. Examples of the $C_2$-$C_{20}$ alkynyl group include a $C_2$-$C_{15}$ alkynyl group, a $C_2$-$C_{10}$ alkynyl group, and a $C_2$-$C_5$ alkynyl group. Examples of the $C_3$-$C_{20}$ aryl group include a $C_3$-$C_{15}$ aryl group, a $C_3$-$C_{10}$ aryl group, and a $C_3$-$C_5$ aryl group.

An amino acid of the compound may be substituted with another amino acid having similar physicochemical properties. Valine (Val), leucine (Leu), tryptophan (Trp), and phenylalanine (Phe) may be substituted with another amino acid having a nonpolar R group, or a derivative thereof. For example, valine (Val) may be substituted with alanine (Ala), leucine (Leu), isoleucine (Ile), phenylalanine (Phe), tryptophan (Trp), or methionine (Met). For example, leucine (Leu) may be substituted with alanine (Ala), valine (Val), isoleucine (Ile), phenylalanine (Phe), tryptophan (Trp), or methionine (Met). For example, tryptophan (Trp) may be substituted with alanine (Ala), valine (Val), leucine (Leu), isoleucine (Ile), phenylalanine (Phe), or methionine (Met). For example, phenylalanine (Phe) may be substituted with alanine (Ala), valine (Val), leucine (Leu), isoleucine (Ile), tryptophan (Trp), or methionine (Met). Threonine (Thr) may be substituted with another amino acid having a polar R group, or a derivative thereof. For example, threonine (Thr) may be substituted with glycine (Gly), serine (Ser), cysteine (Cys), tyrosine (Tyr), asparagine (Asn) or glutamine (Gln).

Trp may be 4-$OCH_3$-Trp, in which a methoxy group is bound to the 4th carbon in the R group.

Phe may be β-OH-Phe in which a hydroxy group is bound to βcarbon.

The compound may be a compound in which an amino group of an amino acid is bound to a $C_1$-$C_{20}$ alkyl group, a $C_1$-$C_{15}$ alkyl group, a $C_1$-$C_{10}$ alkyl group, a $C_1$-$C_5$ alkyl group, or a $C_1$-$C_3$ alkyl group. For example, an amino group of an amino acid of Trp, Leu, Val¹, Val⁵, Thr², or a combination thereof may be bound to a $C_1$-$C_{20}$ alkyl group. Examples of the $C_1$-$C_{20}$ alkyl group include a methyl group.

The compound may be represented by Formula 2:

Formula 2

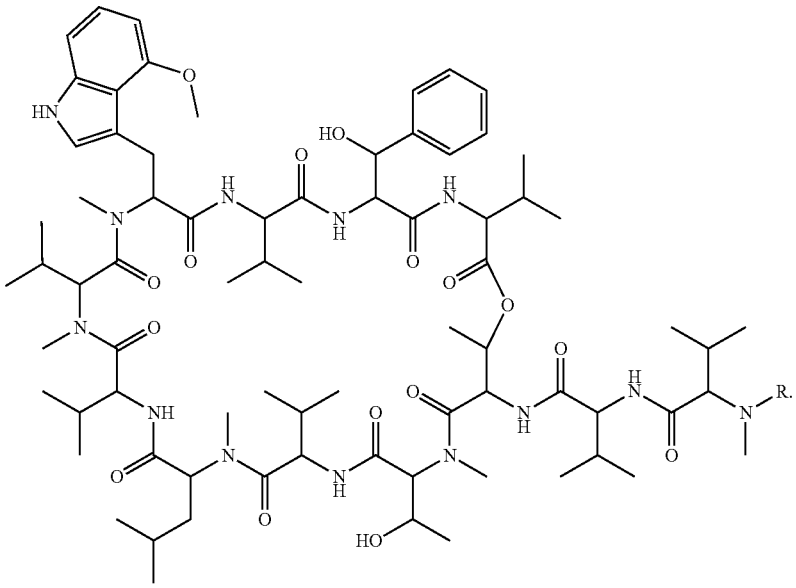

In Formula 2, R may be H, a substituted or unsubstituted $C_1$-$C_{20}$ alkyl group, a substituted or unsubstituted $C_2$-$C_{20}$ alkenyl group, a substituted or unsubstituted $C_2$-$C_{20}$ alkynyl group, a substituted or unsubstituted $C_3$-$C_{20}$ aryl group, or a combination thereof.

The compound may be represented by Formula 3:

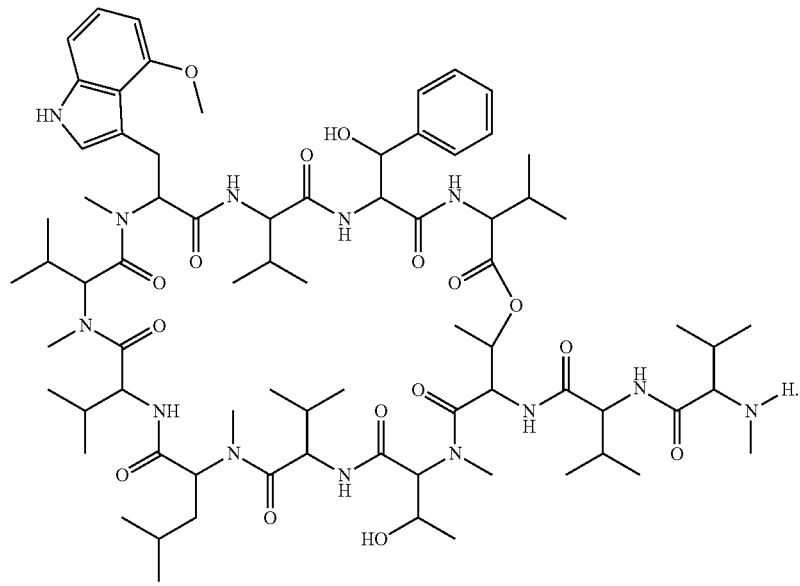

Formula 3

The compound may be represented by Formula 4:

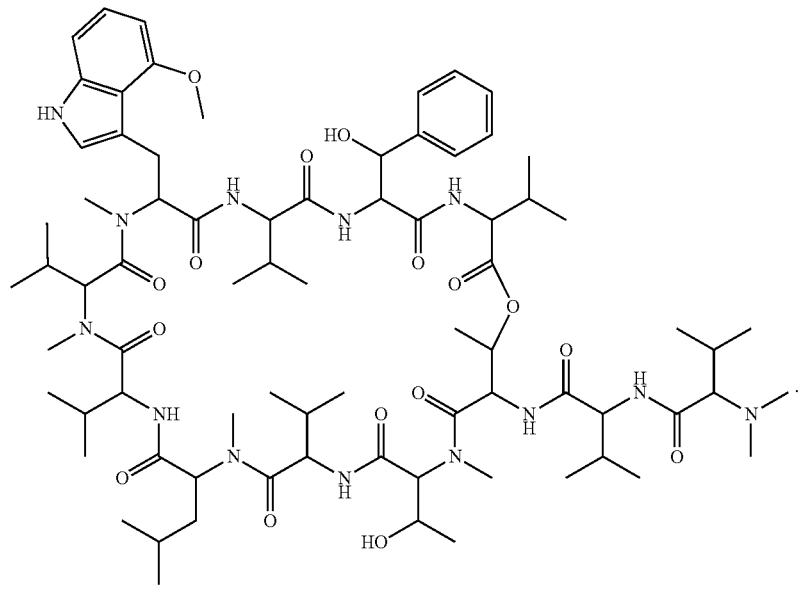

Formula 4

The expression "substituted" as used herein means that a hydrogen atom in an organic compound is substituted with another atomic group to form a derivative. Here, a "substituent" is the atomic group introduced thereto.

Examples of the substituent include a halogen atom, a $C_1$-$C_{20}$ alkyl group substituted with a halogen (e.g., $CCF_3$, $CHCF_2$, $CH_2F$, $CCl_3$, or the like), a $C_1$-$C_{20}$ alkoxy group, a $C_2$-$C_{20}$ alkoxy alkyl group, a hydroxy group, a nitro group, a cyano group, an amino group, an amidino group, hydrazine, hydrazone, a carboxyl group or a salt thereof, a sulfonyl group, a sulfamoyl group, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ heteroalkyl group, a $C_6$-$C_{20}$ aryl group, a $C_6$-$C_{20}$ arylalkyl group, a $C_6$-$C_{20}$ heteroaryl group, a $C_7$-$C_{20}$ heteroaryl alkyl group, a $C_6$-$C_{20}$ heteroaryloxy group, and a $C_6$-$C_{20}$ heteroaryl oxy alkyl group, and a $C_6$-$C_{20}$ heteroaryl alkyl group.

The term "alkyl" as used herein refers to a completely saturated, branched or unbranched (or straight or linear), hydrocarbon. Examples of the $C_1$-$C_{20}$ alkyl group include a $C_1$-$C_{20}$ alkyl group, a $C_1$-$C_{15}$ alkyl group, a $C_1$-$C_{10}$ alkyl group, and a $C_1$-05 alkyl group. Non-limiting examples of alkyl include methyl, ethyl, n-propyl, isopropyl, n-butyl, isobutyl, sec-butyl, n-pentyl, isopentyl, neopentyl, iso-amyl, n-hexyl, 3-methylhexyl, 2,2-dimethylpentyl, 2,3-dimethylpentyl, and n-heptyl.

The term "alkenyl" as used herein refers to a branched or unbranched hydrocarbon having at least one carbon-carbon double bond. Examples of the $C_2$-$C_{20}$ alkenyl group include a $C_2$-$C_{15}$ alkenyl group, a $C_2$-$C_{10}$ alkenyl group, and a $C_2$-$C_5$ alkenyl group. Non-limiting examples of alkenyl include vinyl, allyl, butenyl, isopropenyl, and isobutenyl.

The term "alkynyl" as used herein refers to a branched or unbranched hydrocarbon having at least one carbon-carbon triple bond. Examples of the $C_2$-$C_{20}$ alkynyl group include a $C_2$-$C_{15}$ alkynyl group, a $C_2$-$C_{10}$ alkynyl group, and a $C_2$-$C_5$ alkynyl group. Non-limiting examples of alkynyl include ethynyl, butynyl, isobutynyl, and isopropynyl.

The term "aryl" as used herein include a group in which an aromatic ring is fused to at least one carbon ring. Examples of the $C_6$-$C_{30}$ aryl group include a $C_6$-$C_{15}$ aryl group and a $C_6$-$C_{10}$ aryl group. Non-limiting examples of aryl include phenyl, naphthyl, and tetrahydronaphthyl.

The term "isomer" as used herein refers to a compound with the same molecular formula as another molecule, but with different link or spatial arrangement of constituent atoms in the molecule. The isomer may include, for example, a structural isomer and a stereoisomer. The stereoisomers include diastereomers and enantiomers. An enantiomer, also known as an optical isomer, is one of two stereoisomers that are mirror images of each other that are non-superposable, as one's left and right hands. In case four or more substituents bound to a chiral center carbon of an enantiomer are different from each other, the chiral center is designated R (rectus: clockwise) or S (sinister counterclockwise). Diastereomers are stereoisomers that are not mirror images of each other. Diastereomers include cis-trans isomers having different spatial arrange of atoms.

The term "derivative" as used herein refers to a compound obtained by substituting a part of the structure of a compound with another atom or an atomic group.

The term "solvate" as used herein refers to a compound solvated in an organic or inorganic solvent. For example, the solvate may be a hydrate.

The term "pharmaceutically acceptable salt" as used herein refers to an inorganic and organic acid addition salts of a compound. The pharmaceutically acceptable salt may be a salt that may not cause significant irritation to an organism to which a compound is administered and may not abrogate the biological activity and properties of the compound. The inorganic acid salt may be a salt of hydrochloric acid, bromic acid, phosphoric acid, sulfuric acid, or disulfuric acid. The organic acid salt may be a salt of formic acid, acetic acid, propionic acid, lactic acid, oxalic acid, tartaric acid, malic acid, maleic acid, citric acid, fumaric acid, besylic acid, camsylic acid, edisylic acid, trichloroacetic acid, trifluoroacetic acid, benzoic acid, gluconic acid, methanesulfonic acid, glycolic acid, succinic acid, 4-toluenesulfonic acid, galacturonic acid, embonic acid, glutamic acid, methanesulfonic acid, ethanesulfonic acid, benzenesulfonic acid, p-toluenesulfonic acid, or aspartic acid. The metal salt may be a calcium salt, a sodium salt, a magnesium salt, a strontium salt, or a potassium salt.

The *Mycobacterium* sp. infection may be selected from tuberculosis, leprosy, and nontuberculous mycobacteria (NTM) infection. Tuberculosis is multidrug-resistant (MDR) tuberculosis or extensively drug-resistant (XDR) tuberculosis. MDR tuberculosis may be a form of tuberculosis infection caused by *Mycobacterium tuberculosis* resistant to isoniazid and rifampin. XDR tuberculosis may be a form of tuberculosis infection caused by *Mycobacterium tuberculosis* resistant to quinolone-based injection as well as isoniazid and rifampin.

The related symptom of *Mycobacterium* sp. infection may be cough, chest pain, fever, chills, loss of appetite, weight loss, inflammation, or a combination thereof. For example, the related symptom of *Mycobacterium* sp. infection may be inflammation induced by *Mycobacterium* sp. bacteria.

The *Mycobacterium* sp. bacteria is classified as Corynebacterineae in Actinobacteria. The *Mycobacterium* sp. bacteria may be acid-fast. The *Mycobacterium* sp. bacteria may be, for example, *Mycobacterium tuberculosis, Mycobacterium bovis, Mycobacterium africanum, Mycobacterium microti,* or *Mycobacterium leprae*.

The compound including a peptide represented by Formula 1, or an isomer, a derivative, a solvate, or a pharmaceutically acceptable salt thereof may promote autophagy of macrophage, palliate inflammation, or induce a combination thereof.

The composition may further include antibiotics. The antibiotics may be antituberculosis drug. For example, the antituberculosis drug may be isoniazid, rifampicin, ethambutol, SQ-109, pyrazinamide, streptomycin, kanamycin, capreomycin, ethionamide, prothionamide, enviomycin, para-aminosalicylic acid, cycloserine, amikacin, levofloxacin, moxifloxacin, gatifloxacin, ofloxacin, terizidone, thionamide, ethionamide, protionamide, clofazimine, linezolid, amoxicillin, clavulanate, thioacetazone, imipenem, cilastatin, clarithromycin, bedaquiline, delamanid, Imipenem, cilastatin, meropenem, or a combination thereof. The compound including a peptide represented by Formula 1, or an isomer, a derivative, a solvate, or a pharmaceutically acceptable salt thereof and the antibiotics may be a single composition or separate compositions.

The term "prevention" as used herein refers to any actions by which a disease is inhibited or onset of a disease is retarded by administration of a composition. The term "treatment" as used herein refers to any actions by which the symptoms of a disease have taken a turn for the better or been modified favorably by administration of a composition.

The pharmaceutical composition may further include a carrier, excipient, or a diluent. Such a carrier, an excipient, or a diluent may be, for example, lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinyl pyrrolidone, water, methyl hydroxybenzoate, propyl hydroxybenzoate, talc, magnesium stearate, or mineral oil.

The pharmaceutical composition may be formulated in the form of oral preparations such as powders, granules, tablets, capsules, suspensions, emulsions, syrups, and aerosols, external preparations, suppositories, or sterilized injection solutions, according to a conventional method. In the case of formulation, a diluent or an excipient, e.g., a filler, an extender, a binder, a wetting agent, a disintegrant, and a surfactant, which are typically used, may be used.

Regarding the pharmaceutical composition, solid preparations for oral administration may be tablets, pills, powders, granules, or capsules. The solid preparations may further include an excipient. Such an excipient may be, for example, starch, calcium carbonate, sucrose, lactose, or gelatin. In addition, the solid preparations may further include a lubricant, such as magnesium stearate or talc. Regarding the pharmaceutical composition, solution preparations for oral administration may be suspensions, liquids, emulsions, or syrups. The solution preparations may include water or liquid paraffin. The liquid preparations may include an excipient, such as a wetting agent, a sweetening agent, an air freshener, or a preservative. Regarding the pharmaceutical composition, preparations for parenteral administration may be sterilized aqueous solutions, non-aqueous solutions, suspensions, emulsions, freeze-dried preparations, or suppositories. Non-aqueous solutions or suspensions may include vegetable oils or esters. Vegetable oils may include, for example, propylene glycol, polyethylene glycol, or olive oil. Esters may include, for example, ethyl oleate. A base of the suppository may be witepsol, macrogol, tween 61, cacao butter, laurin butter, or glycerogelatin.

A preferred dosage of the pharmaceutical composition varies depending on the conditions and weight of a subject, a degree of disease, drug form, and administration route and period, but may be appropriately chosen by one of ordinary skill in the art. For example, the compound, or an isomer, a derivative, a solvate, or a pharmaceutically acceptable salt thereof may be administered in an amount of about 0.0001 milligrams per kilograms (mg/kg) to about 100 mg/kg, or about 0.001 mg/kg to about 100 mg/kg 1 to 24 times per day, 1 to 7 times per 2 to 7 days, or 1 to 24 times per 1 to 12 months. In the pharmaceutical composition, the compound, or an isomer, a derivative, a solvate, or a pharmaceutically acceptable salt thereof may be included in an amount of about 0.0001 percent by weight (wt %) to about 10 wt %, or about 0.001 wt % to about 1 wt %, based on the total weight of the composition.

The pharmaceutical composition may be administered via an oral or parental route. The pharmaceutical composition may be administered, for example, via an oral, transdermal, subcutaneous, rectal, intravenous, intraarterial, intraperitoneal, intramuscular, intrasternal, topical, intranasal, intratracheal, or intradermal route. The pharmaceutical composition may be administered systemically or topically, singly or together with another pharmaceutically active compound.

Another aspect of the present disclosure provides a method of treating or preventing *Mycobacterium* sp. infection or a related symptom thereof, the method including administering the pharmaceutical composition according to the other aspect into a subject.

The subject, e.g., may be humans, cattle, horses, pigs, dogs, sheep, goats, or cats. The subject may be a subject having *Mycobacterium* sp. infection or a related symptom thereof or high possibility of having the same.

The method may further include administering antibiotics to the subject. The antibiotics may be administered concurrently, individually, or sequentially with the compound including a peptide represented by Formula 1, or an isomer, a derivative, or a pharmaceutically acceptable salt thereof to the subject.

The administration method may be an oral or parental administration. The administration method may be, for example, via an oral, transdermal, subcutaneous, rectal, intravenous, intraarterial, intraperitoneal, intramuscular, intrasternal, topical, intranasal, intratracheal, or intradermal route. The pharmaceutical composition may be administered systemically or topically, singly or together with another pharmaceutically active compound.

A preferred dosage of the pharmaceutical composition varies depending on the conditions and weight of a subject, a degree of disease, drug form, and administration route and period, but may be appropriately chosen by one of ordinary skill in the art. The administration dose may be, for example, in a range of about 0.001 mg/kg to about 100 mg/kg, about 0.01 mg/kg to about 10 mg/kg, or about 0.1 mg/kg to about 1 mg/kg for adults, once per day, several times per day, once per week, once per 2 weeks, once per 3 weeks, or once per 4 weeks to once per year.

The term "including or comprising" as used herein is construed as meaning that it is possible to add and/or intercalate other components, rather than excluding other components, unless otherwise stated.

The present disclosure will be described in further detail with reference to the following examples. However, these Examples are for illustrative purposes only, and the scope of the present disclosure is not intended to be limited by these Examples.

Example 1. Test of Anti-*Mycobacterium tuberculosis* Activity of Ohmyungsamycins (OMS)

1. Incubation of Genus *Streptomyces* SNJ042 Strain

A marine-derived bacterium, a genus *Streptomyces* SNJ042 strain, was prepared (Korean Patent No. 10-1522625 (Granted on 18, May, 2015)).

The genus *Streptomyces* SNJ042 strain was inoculated in a YEME solid medium (including 10 grams (g) of malt extract, 4 g of yeast extract, 2 g of glucose, 34 g of artificial sea salt, and 18 g of agar per 1 liter (L) of water), and then was subjected to a primary incubation at a temperature of 30° C. for about 14 days.

Subsequently, spores produced by the strain 125 milliliters (ml) was inoculated in a YEME liquid medium (including 10 g of malt extract, 4 g of yeast extract, 4 g of glucose, and 34 g of artificial sea salt per 1 L of water), and then was subjected to shaking-incubation at a temperature of about 28° C. at a rate of about 180 revolutions per minute (rpm) for about 2 days. 14 ml of the culture solution was inoculated in 1 L of A1+C liquid medium (10 g of starch, 4 g of enzyme extract, 2 g of peptone, 1 g of calcium carbonate, and 34 g of artificial sea salt per 1 L of water), and then was subjected to shaking-incubation at a temperature of about 28° C. at a rate of about 180 rpm for about 6 to about 7 days.

Total 108 liquid media of 1 L were inoculated in 108 of the strains, and consequently, the genus *Streptomyces* SNJ042 strain was incubated in 108 L of the liquid medium.

2. Separation of OMS

1 L of the SNJ042 strain culture solution incubated as in Section 1 and 1.5 L of ethyl acetate were poured into a separation funnel. The inlet of the separation funnel was sealed, followed by intense mixing for about 2 minutes to mix the solution. Subsequently, the mixture was allowed to stand for about 1 minute 2 times repeatedly, and then was allowed to stand for 3 minutes. Next, a layer of water was removed therefrom to obtain an ethyl acetate layer. 100 g of anhydrous sodium sulfate was added to the obtained ethyl acetate layer to remove water therefrom. Subsequently, the ethyl acetate layer was filtered using a filter paper. The filtrate was subjected to a reduced pressure to remove ethyl acetate by evaporation, and then the solution was concentrated. By repeating this process, 12 g of crude extract was obtained from 108 L of the culture solution.

The crude extract underwent two times of reversed-phase chromatography (SEPAK® $C_{18}$ 20 g) to thereby fractionate the crude extract into 5 fractions. For the fractions, solvents of water and methanol were used. In particular, 200 ml of 20% (v/v), 40% (v/v), 60% (v/v), 80% (v/v), and 100% (v/v) methanol/water solutions were used. Fractionation started using a 20% (v/v) methanol/water solution, and continued while raising a concentration of methanol (from 20% (v/v) methanol/water to 100% (v/v) methanol). Once the fractionation using 100% (v/v) methanol was complete, 20 microliters (μl) of 200 ml of 5 fractions were each moved to vials for liquid chromatography/mass spectrometry (LC/MS) analysis to analyze the fractions using LC/MS. In the analysis, a reversed-phase high-performance liquid chromatography (HPLC) column (available from Phenomenex, $C_{18}$ (2), 100×4.6 mm) was used under a concentration gradient solvent condition (from 10% (v/v) to 100% (v/v) of acetonitrile/water for 20 minutes). By using the retention time ($t_R$), an ultraviolet (UV) ray spectrum, and a mass spectrum, Fraction 4 (80% (v/v) methanol/water) and Fraction 5 (100% (v/v) methanol/water) were found to include target materials, OMS-A and OMS-B.

Fractions 4 and 5 were concentrated using a vacuum evaporator and dissolved in 100% (v/v) methanol, followed by separation using the reversed-phase HPLC column (available from Kromacil, $C_{18}$ (2), 250×10 mm) under a concentration gradient solvent condition (from 40% (v/v) to 56% (v/v) acetonitrile/water for 20 minutes, and then 60% (v/v) acetonitrile/water). OMS-A and OMS-B compounds were respectively eluted about 32 minutes and about 34 minutes after the HPLC injection under the aforementioned separation conditions. A purity of each of the obtained OMS-A and OMS-B was identified by using LC/MS as described above. Finally, 70 mg of pure OMS-A and 20 mg of pure OMS-B were separated.

3. Measurement of Minimum Inhibitory Concentration (MIC) of OMS Against *Mycobacterium tuberculosis*

In order to test whether OMS-A and OMS-B inhibits activity of *Mycobacterium tuberculosis* (Mtb), a MIC of each of OMS-A and OMS-B was measured.

In order to measure the MIC of each of OMS-A and OMS-B, resazurin-based microtiter plate assay (REMA) was performed. An Mtb H37Rv strain (University of Arizona) was prepared, the prepared Mtb H37Rv strain was diluted and cultured such that an $OD_{600}$ value was 0.005. 100 μl of the Mtb H37Rv strain culture solution was inoculated in each well of the 96-well plate.

OMS-A and OMS-B prepared in Section 2 were used as for sample compounds. As for a positive control, isoniazid (INH) (available from Sigma) and ethambutol (EMB) (available from Sigma), which are antibiotics used as antituberculosis drugs, and SQ109 (available from Sigma) (Stehr et al., *Curr. Top. Med. Chem.*, 2014, vol. 14, p. 110-129), which is under development as a antituberculosis drug, were used. These compounds were diluted by two-fold serial dilutions. The prepared compounds and 40 μl of a 0.025% (w/v) resazurin (available from Sigma) solution were added to each well, and each plate was incubated at a temperature of about 37° C. for about 5 days.

After 1 day of incubation, the amount of resorufin, which is a metabolite of resazurin, was measured using a Synergy H1 micro plate reader (available from BioTek). Based on the amount of resorufin measured by using GraphPad Prism 5.0 software, $MIC_{50}$ (bacterial growth 50% MIC) was measured. The relative fluorescence unit (RFU) measured depending on a concentration of the compounds are shown in FIG. 2.

Figure 2:
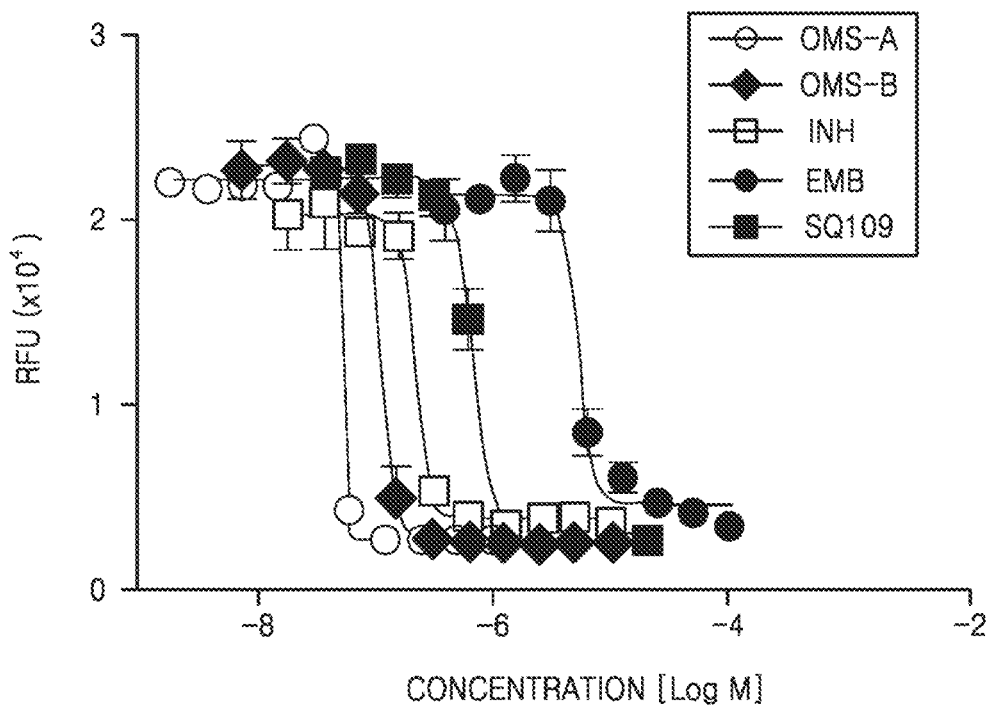
FIG. 2 is a graph that illustrates anti-*Mycobacterium tuberculosis* activity depending on a concentration of each compound ("○" represents OMS-A, "♦" represents OMS-B, "□" represents INH, "●" represents EMB, "■" represents SQ109, and "RFU" represents a relative fluorescence unit)

As shown in FIG. 2, the OMS-A and OMS-B compounds have excellent anti-*Mycobacterium tuberculosis* activity, as compared with INH, EMB, and SQ109. The $MIC_{50}$ of each of OMS-A and OMS-B Compounds were 57 nanomolar (nM) and 117 nM, respectively.

4. Antibacterial Activity of OMS Against Macrophage Infected with *Mycobacterium tuberculosis*

Bone-marrow-derived macrophages (BMDM) taken from a wild-type mouse (Samtako Bio Korea Co., Ltd.) were cultured in a plate. 10 multiplicity of infection (MOI) of the Mtb H37Rv strain was added to the cultured macrophage, followed by incubation at a temperature of about 37° C. for about 4 hours under a 5% $CO_2$ condition.

Figure 3A:
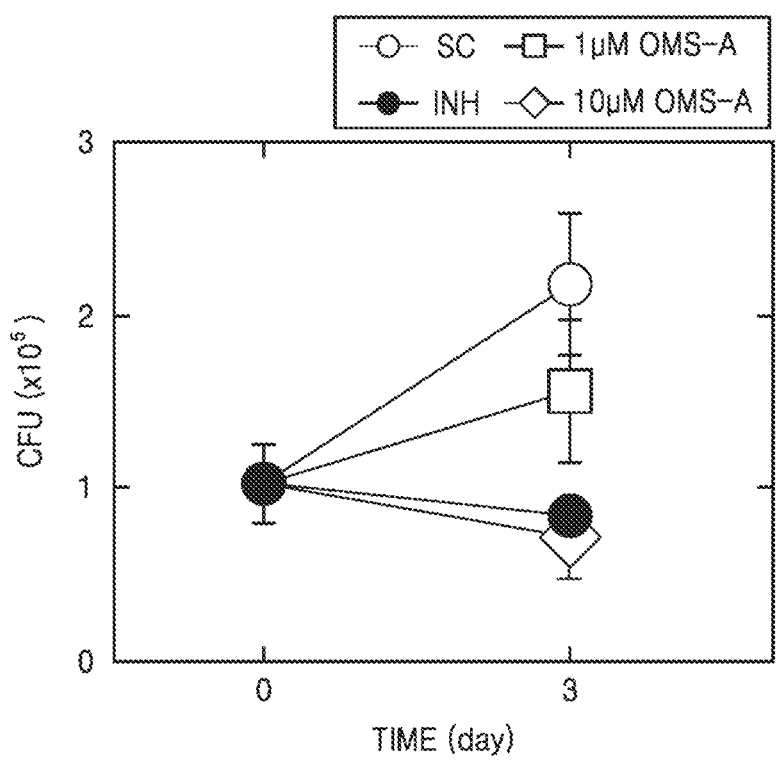
FIG. 3A is a graph of colony forming unit (CFU) versus incubation time (day) upon addition of OMS-A.
Figure 3B:
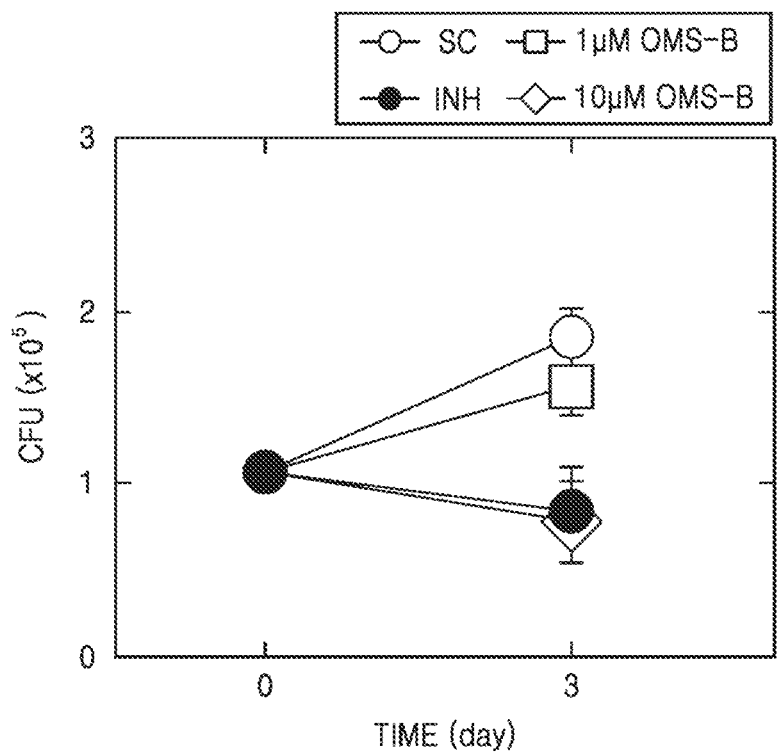
FIG. 3B is a graph of CFU versus incubation time (day) upon addition of OMS-B.
Figure 4:
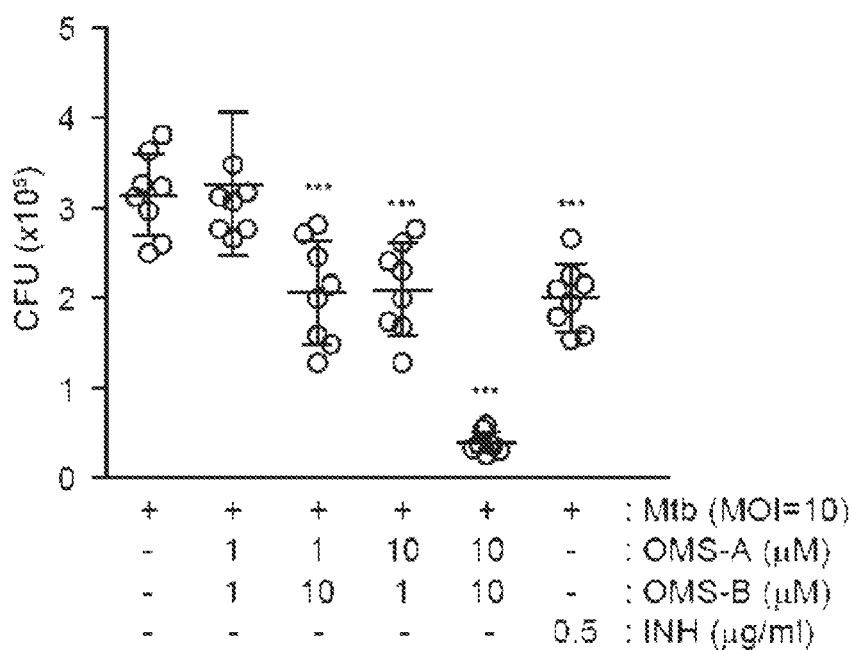
FIG. 4 is a graph of CFU versus a concentration of OMS-A, OMS-B, or a combination thereof.

1 micromolar (μM) or 10 μM of OMS-A, 1 μM or 10 μM of OMS-B, or a combination thereof was added to the macrophage infected with *Mycobacterium tuberculosis*, followed by incubation at a temperature of about 37° C. for about 3 days under a 5% $CO_2$ condition. As for a negative control, a solvent control (SC), which was not added with OMS-A or OMS-B, was used. As for a comparison group, 0.5 micrograms per microliter (μg/ml) of INH (available from Sigma) was used. The colony forming unit (CFU) of the incubated macrophage was measured. Upon addition of OMS-A and OMS-B, the changes of CFU over time (incubation time (day)) are shown in FIGS. 3A and 3B. Further, a combination of OMS-A and OMS-B was added thereto and incubated for 3 days. The CFU difference depending on a concentration of the added compound is shown in FIG. 4 (***: $p<0.001$).

As shown in FIGS. 3A and 3B, a CFU of each of OMS-A and OMS-B was similar as that of INH, and decreased in a concentration-dependent manner. Also, as shown in FIG. 4, treatment with OMS-A and OMS-B together have resulted in a low CFU. Therefore, it was found that OMS-A and OMS-B have antibacterial activity against a macrophage infected with *Mycobacterium tuberculosis*.

5. Antibacterial Activity of OMS In Vivo

In order to test whether OMS has antibacterial activity in vivo, *Mycobacterium marinum*-*Drosophila melanogaster* infection system was used (Dionne et al., *Infect Immun.*, 2003, vol. 71, p. 3540-3550).

Figure 5A:
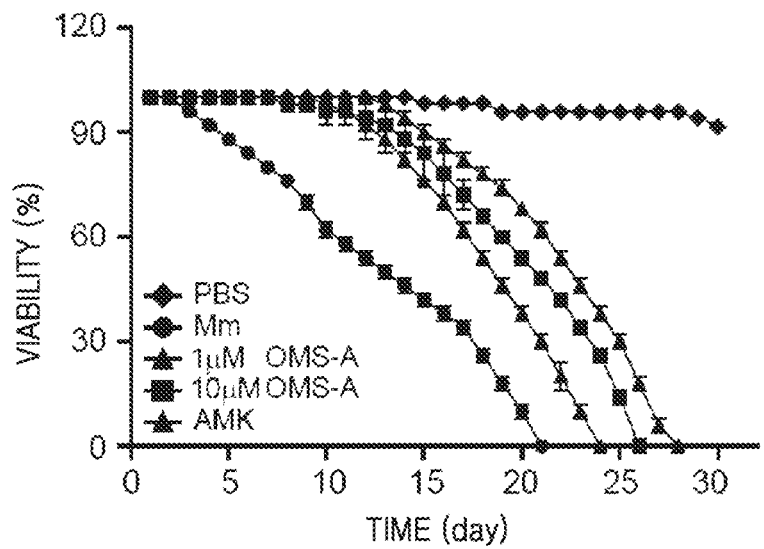
FIG. 5A is a graph of viability (percent, %) of *Drosophila melanogaster* infected with *Mycobacterium marinum* depending on a concentration of OMS-A.

*Drosophila melanogaster* was inhaled with $CO_2$ gas and infected with *M. marinum* adjusted to have 500 CFUs. *Drosophila melanogaster* were then cultured in a culture medium containing 1 μM or 10 μM of OMS-A. The survival rate was calculated by counting the number of *Drosophila melanogaster* for about 30 days after transferring to a new culture medium every 3 days. Phosphate-buffered saline (PBS) was added to *Drosophila melanogaster* not infected with *M. marinum* as a positive control, and *Drosophila melanogaster* infected with *M. marinum* was used as a negative control. In addition, as for a comparison group, amikacin (AMK, available from Sigma), which is an antibiotic of 1 μg/ml, was added to *Drosophila melanogaster* infected with *M. marinum*. The calculated viabilities (%) of *Drosophila melanogaster* are shown in FIG. 5A ("Mm" represents *Drosophila melanogaster* infected with *M. marinum*). As shown in FIG. 5A, OMS-A as well as AMK increased viability of *Drosophila melanogaster* infected with *M. marinum*.

Figure 5B:
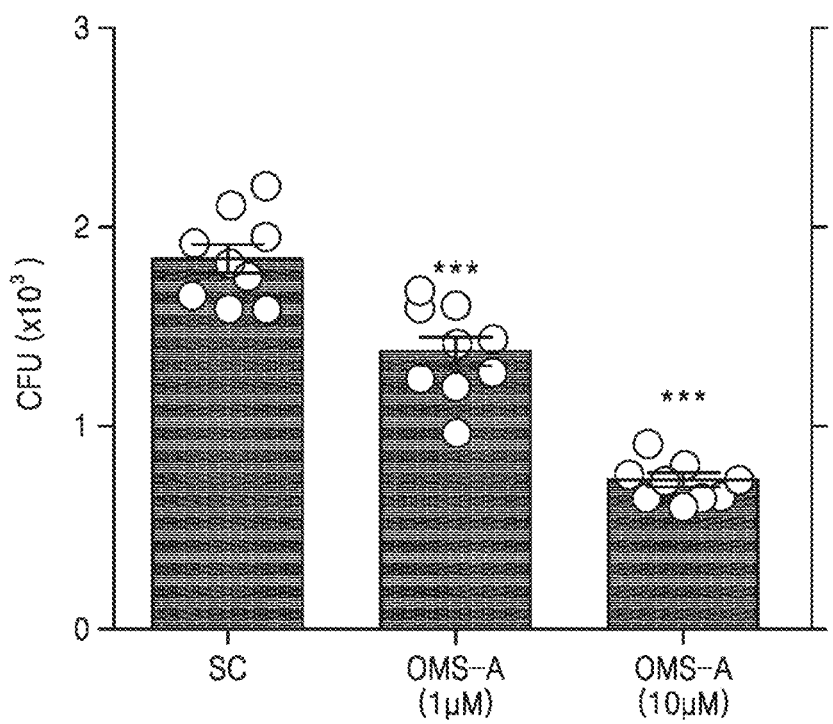
FIG. 5B is a graph of CFU of *M. marinum* present in *Drosophila melanogaster*.

For more accurate results, *Drosophila melanogaster* were anesthetized and transferred to a new tube, and homogenized using a homogenizer until only the cuticle layer remained. Then, *M. marinum* present in *Drosophila melanogaster* was extracted and the CFU was measured as described in Section 4. The CFUs of *M. marinum* present in *Drosophila melanogaster* depending on a concentration of OMS-A are shown in FIG. 5B (***: p<0.001). As shown in FIG. 5B, in the case of treatment with OMS-A, the CFUs of *M. marinum* present in *Drosophila melanogaster* decreased in a concentration-dependent manner, as compared with the negative control, which is a SC.

Therefore, it was found that OMS-A has antibacterial activity in vivo as well as in vitro.

6. Effect of OMS on Activation of Macrophage Autophagy

It was tested whether OMS-A and OMS-B are involved in the activation of macrophage autophagy.

Figure 6A:
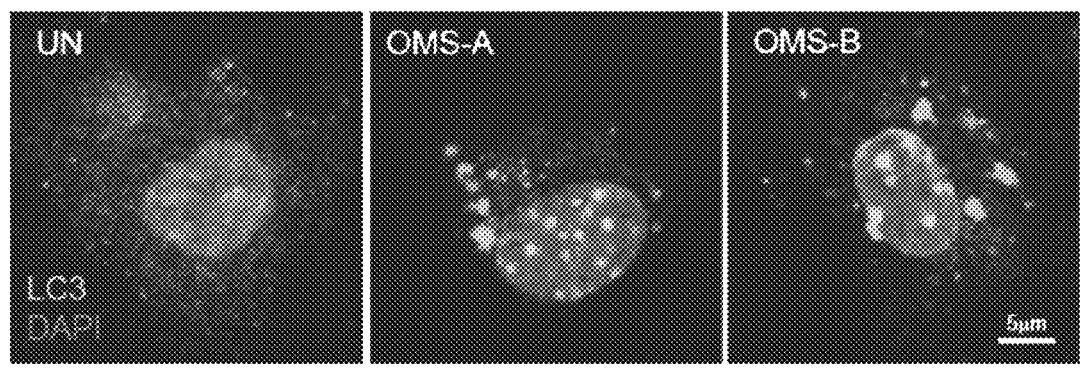
FIG. 6A are images of macrophages stained with DAPI and anti-LC3 antibody, depending on the presence of OMS-A or OMS-B.
Figure 6B:
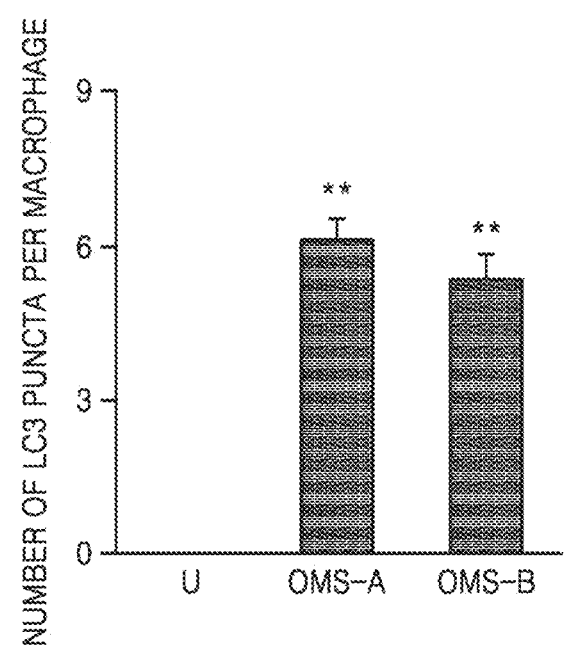
FIG. 6B is a graph of the number of LC3 puncta per macrophage, depending on the presence of OMS-A or OMS-B.

LC3 puncta formation and lipidation assay (Eisuke and Noboru, Autophagy, 2010, vol. 6, p. 764-776), which is mainly used in macrophage autophagy measurement, was performed. 10 μM of OMS-A or 10 μM of OMS-B was added to BMDM prepared in Section 4, and then cultured for about 24 hours. As a negative control, PBS was used. Subsequently, macrophage was stained with 4',6-diamidino-2-phenylindole (DAPI, available from Sigma) and anti-LC3 antibody (available from Cell Signaling), and the number of LC3 puncta per macrophage was measured. The images of the stained macrophages are shown in FIG. 6A ("UN" represents "untreated"), and the number of LC3 puncta per macrophage are shown in FIG. 6B (**: p<0.01). As shown in FIGS. 6A and 6B, in the case of treatment with OMS-A and OMS-B, LC3 puncta formation was great.

Figure 7A:
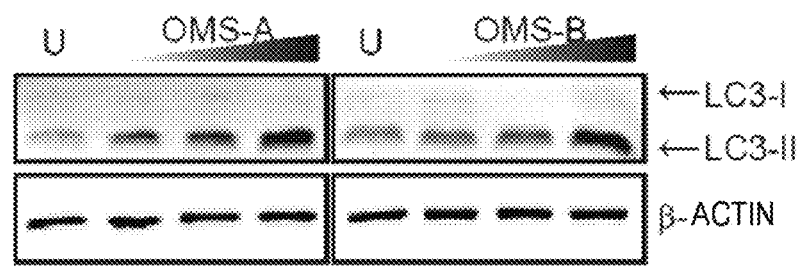
FIG. 7A are each an immuloblotting images of macrophages in the presence of OMS-A or OMS-B.
Figure 7B:
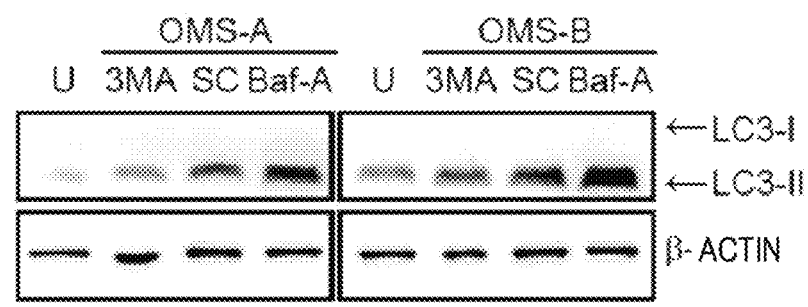
FIG. 7B are each an immuloblotting images of macrophages upon pre-treatment with 3-methyladenine (3-MA) or Bafilomycin A1 (Baf-A)

In addition, 1 μM, 5 μM, and 10 μM of OMS-A or OMS-B were added to a macrophage and cultured for about 24 hours, to thereby obtain cytolysate of the macrophage. The obtained cytolysate was subjected to immunoblotting using anti-LC3 antibody (available from Cell Signaling) and anti-β-actin antibody (available from Santa Cruz). The results thereof are shown in FIG. 7A ("U" represents "untreated"). Further, in the case of pre-treatment of a macrophage with 10 μM of 3-methyladenine (3-MA), which is an autophagy inhibitor, or 100 nM of Bafilomycin A1 (Baf-A), which is an $H^+$-ATPase inhibitor, the immunoblot images of the macrophage are shown in FIG. 7B ("U" represents "untreated", and "SC" represents "solvent control"). As shown in FIG. 7A, in the case of treatment with OMS-A and OMS-B, the amount of LC3-II, which is LC2-phosphatidyl ethanolamine conjugate, increased as compared with LC3-I, which is a cytosolic form of LC3. As shown in FIG. 7B, in the case of pre-treatment with 3-MA, the amount of LC3-II decreased, as compared with the case of treatment with OMS-A or OMS-B. In the case of pre-treatment with Baf-A, the amount of LC3-II increased, as compared with the case of treatment with OMS-A or OMS-B.

Figure 8:
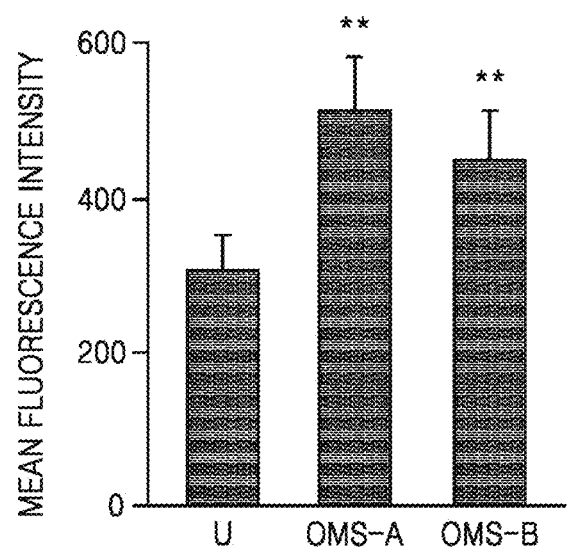
FIG. 8 is a graph illustrating results of analysis of flow cytometry on macrophages treated with OMS-A or OMS-B.

10 μM of OMS-A or OMS-B was added to a macrophage, and then cultured for about 24 hours. Subsequently, a mean fluorescence intensity (MFI) of the macrophage was measured using the anti-LC3B antibody (available from Cell Signaling) according to flow cytometry. The MFIs in the case of treatment with OMS-A and OMS-B are shown in FIG. 8 (**: p<0.01). As shown in FIG. 8, the macrophage treated with OMS-A and OMS-B was found to have in increased level of LC3B expression.

Therefore, it was found that OMS-A and OMS-B improve autophagy.

Figure 9:
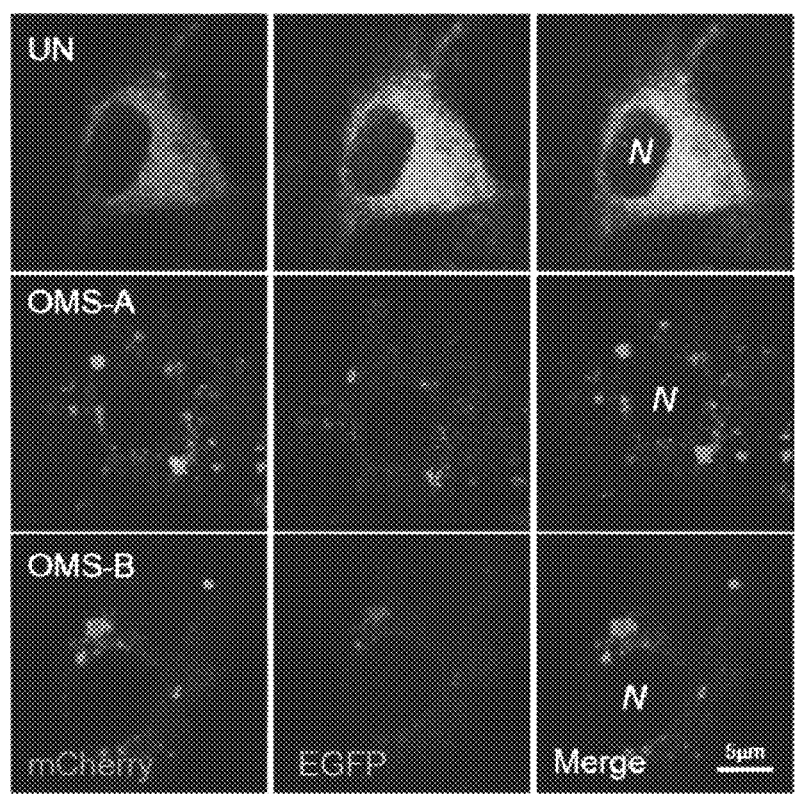
FIG. 9 are immunofluorescent staining images of macrophages treated with OMS-A or OMS-B.

Further, a macrophage was transfected with a retrovirus vector that expresses mCherry-enhanced green fluorescent protein (EGFP)-LC3B. 10 μM of OMS-A or OMS-B was added to the transfected macrophage and then incubated for about 24 hours. Fluorescent images of the transfected macrophage were obtained, which are shown in FIG. 9 ("UN" represented "untreated", and "N" represents "nucleus"). As shown in FIG. 9, upon measurement of fluorescence intensity of mCherry-EGFP-LC3B transferred to a lysosome of the macrophage, the number of red puncta increased. Therefore, it was found that OMS-A and OMS-B enhances autophagic flux as well as autophagy.

7. Effect of OMS on Inflammatory Response of Macrophage Induced by *Mycobacterium tuberculosis*

In order to test whether OMS-A and OMS-B inhibits maturation of phagolysosome induced by Mtb, a macrophage was prepared as in Section 4.

Figure 10A:
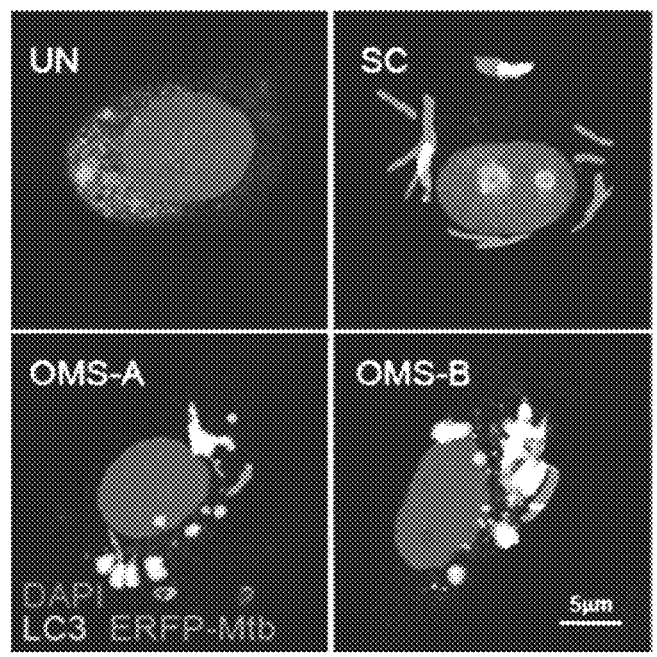
FIG. 10A are fluorescent images obtained for LC3.
Figure 10B:
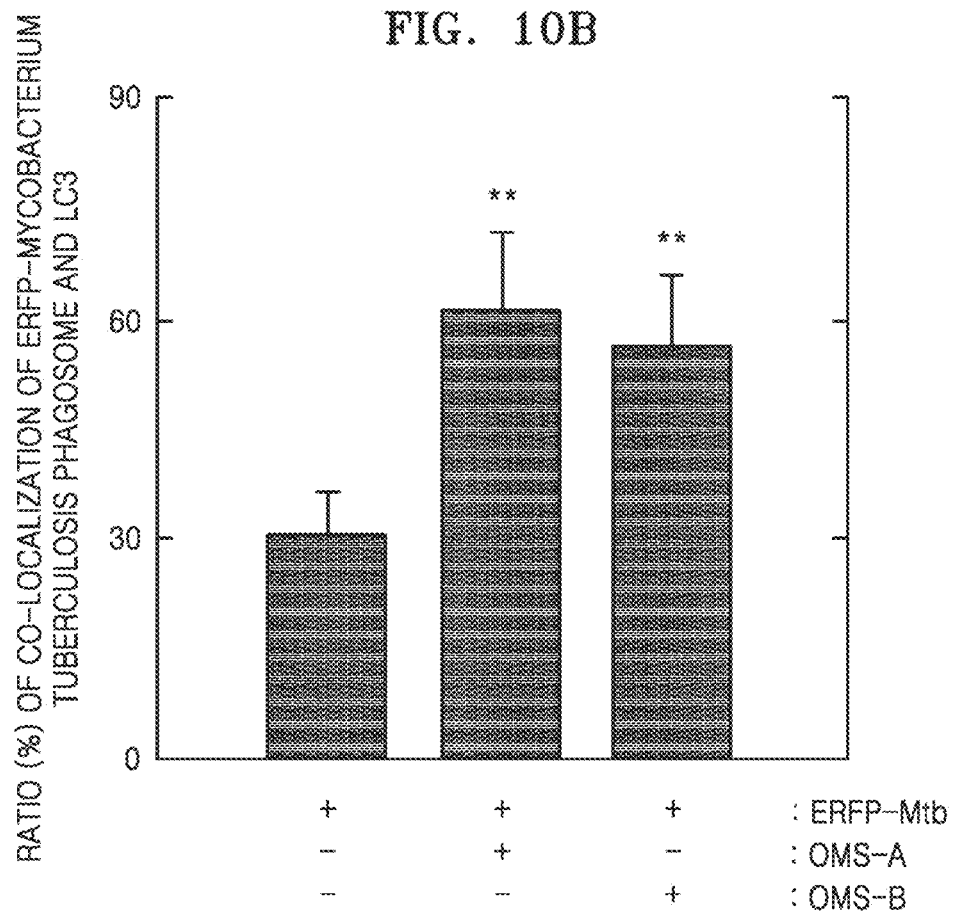
FIG. 10B is a graph of ratio (%) of co-localization of ERFP-*Mycobacterium tuberculosis* (Mtb) phagosome and LC3.
Figure 10C:
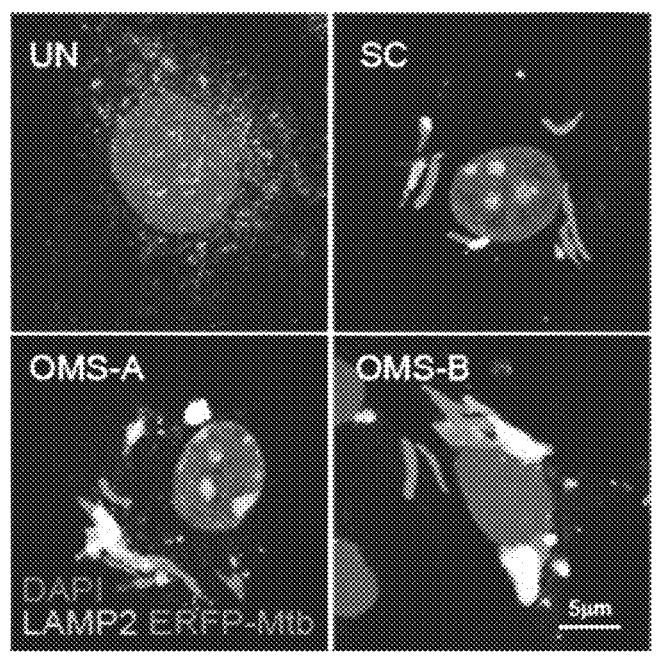
FIG. 10C are fluorescent images obtained for LAMP2.
Figure 10D:
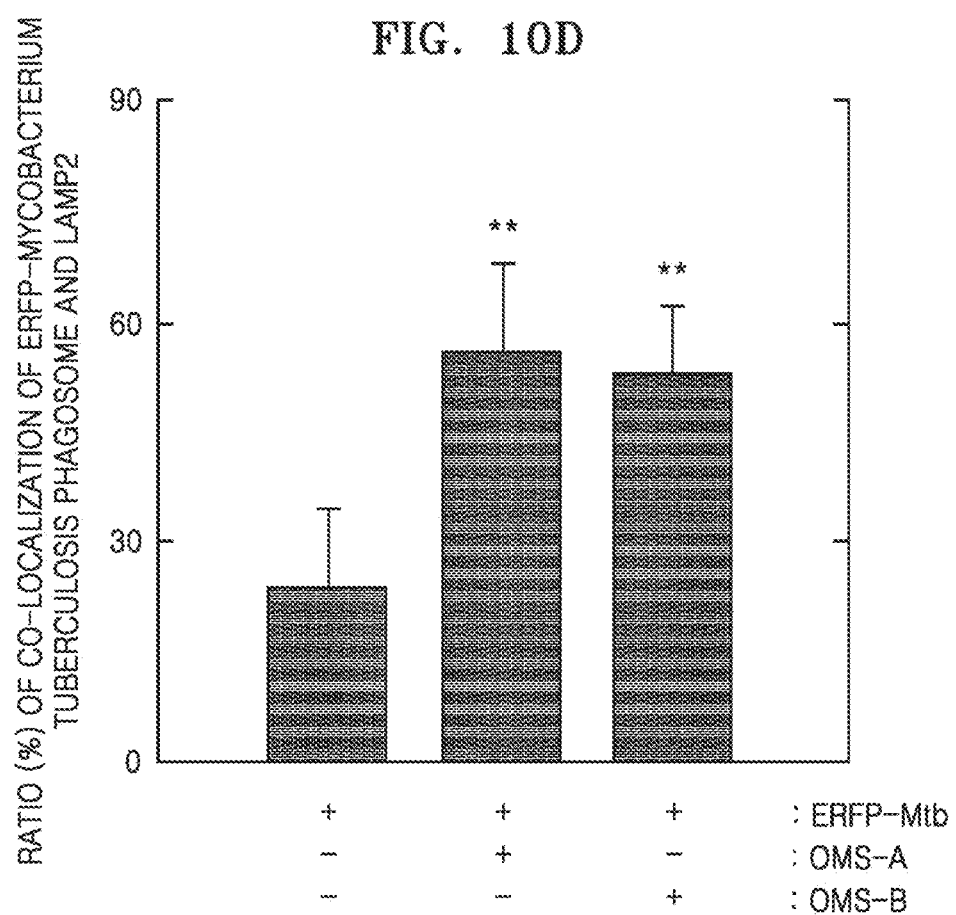
FIG. 10D is a graph of ratio (%) of co-localization of Mtb phagosome and LAMP2.

The prepared macrophage was transfected with an enhanced red fluorescent protein (ERFP)-Mtb (available from University of Gyeongsang), and then added with 10 μM of OMS-A or OMS-B. After incubating the macrophage for about 24 hours, an anti-LC3 antibody (MBL), an anti-lysosome-associated membrane protein 2 (LAMP2) antibody (available from Santa Cruz), and DAPI were used to thereby obtain the fluorescent images of the macrophage. A ratio (%) of co-localization of Mtb phagosome and LC3 or LAMP2 was calculated from the obtained fluorescent image. The obtained fluorescent image for LC3 and a ratio of co-localization of Mtb phagosome and LC3 are respectively shown in FIGS. 10A and 10B. The obtained fluorescent image for LAMP2 and a ratio of co-localization of Mtb phagosome and LAMP2 are respectively shown in FIGS. 10C and 10D. (**: p<0.01).

As shown in FIGS. 10A to 10D, in the case of treatment with OMS-A and OMS-B, co-localization of LC3 and Mtb phagosome and co-localization of LAMP2 and Mtb phagosome, which are indexes for autophagy, increased Therefore, it was found that OMS-A and OMS-B induce maturation of Mtb phagosome in a macrophage.

8. Effects of OMS on AMPK Pathway Necessary for Maturation of Mtb Phagosome in Macrophage and Antibacterial Response It is known that activation of an AMP-activated protein kinase (AMPK) induces maturation of Mtb phagosome in a macrophage and an antibacterial response. Thus, it was tested whether OMS-A and OMS-B induces activation of AMPK cell signaling pathway.

OMS-A and OMS-B were added to an Mtb-infected macrophage, as prepared in Section 4, and then incubated for about 18 hours. Cell lysate was obtained from the cultured cells, and an anti-p-AMPK catalytic α-subunit (AMPK-α) Thr172 (T172) antibody (available from Cell Signaling), an anti-p-acetyl-CoA carboxylase (ACC) antibody (available from Cell Signaling), and an anti-β actin antibody (available from Cell Signaling) were used to perform immunoblotting. The immunoblotting images for OMS-A and OMS-B are respectively shown in FIGS. 11A and 11B.

Figure 11A:
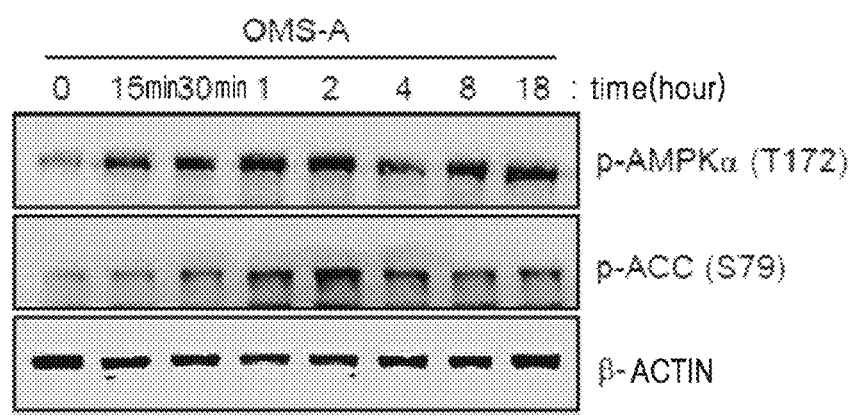
FIG. 11A is an immunoblotting image obtained using OMS-A.
Figure 11B:
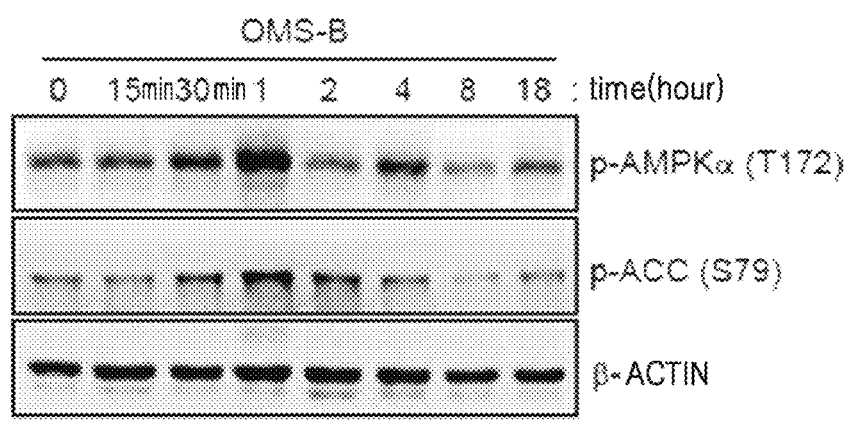
FIG. 11B is an immunoblotting image obtained using OMS-B.

As shown in FIGS. 11A and 11B, OMS-A and OMS-B induced phoshorylation in Thr172 of AMPKα and Ser78 (S79) of ACC in a time-dependent manner. In particular, in a case where a macrophage is treated with OMS-A or OMS-B, AMPK phoshorylation rapidly increased within about 1 hour and then gradually decreased. After a lapse of about 18 hours, it was found that phoshorylation was induced.

9. Alleviation of OMS on Inflammatory Response Induced by *Mycobacterium tuberculosis*

As described in Section 4, 1 μM, 5 μM, or 10 μM of OMS-A and OMS-B were added to an Mtb-infected macrophage, and then incubated for about 24 hours.

The incubated macrophage was obtained, the amounts of tumor necrosis factor (TNF)-α, interleukin (IL)-6, IL-1β, and IL-12 p40 secreted from the macrophage were measured using an ELISA kits (available from BD).

Figure 12A:
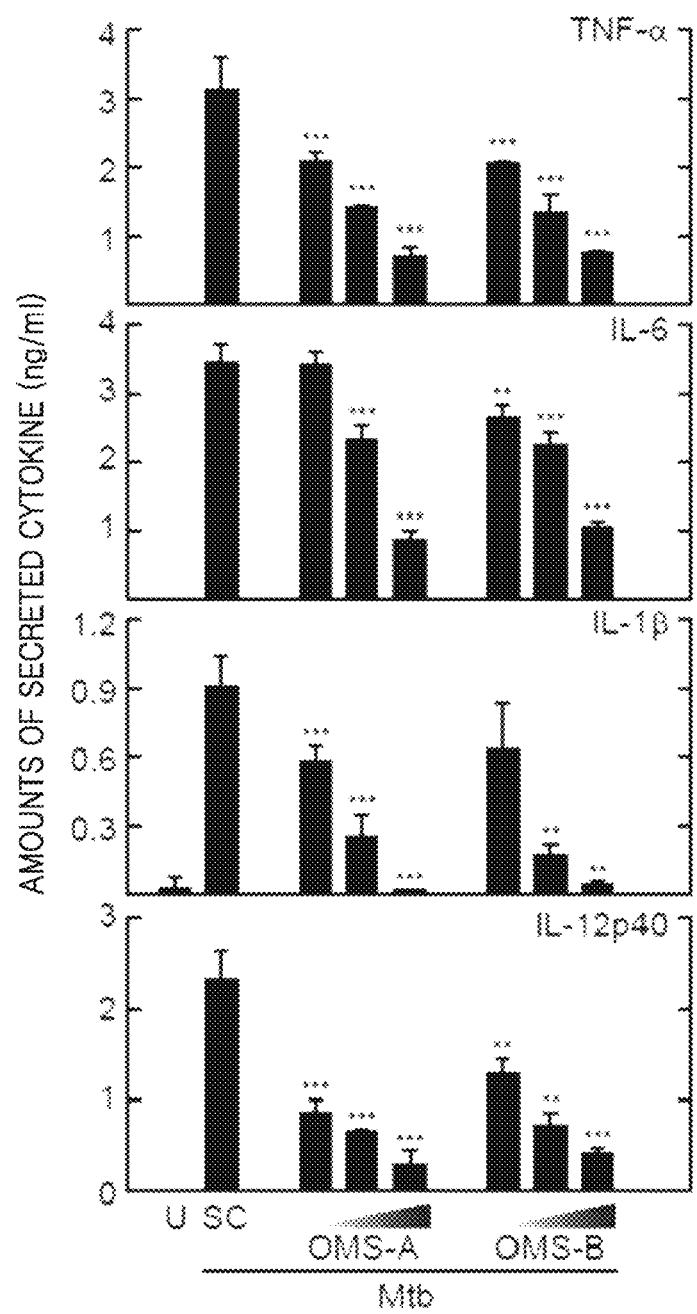
FIG. 12A are graphs of amounts of cytokine secreted from Mtb-infected macrophages depending on amounts of OMS.

The amount of cytokine secreted from Mtb-infected macrophage versus the amount of OMS is shown in FIG. 12A ("U" represents "untreated", "SC" represents" "solvent control", *: p<0.001, and : p<0.01). As shown in FIG. 12A, in the case of treatment of the Mtb-infected macrophage with OMS-A or OMS-B, the amount of TNF-α, IL-6, IL-1β, and IL-12 p40, which are proinflammatory cytokine, decreased in a concentration-dependent manner.

Figure 12B:
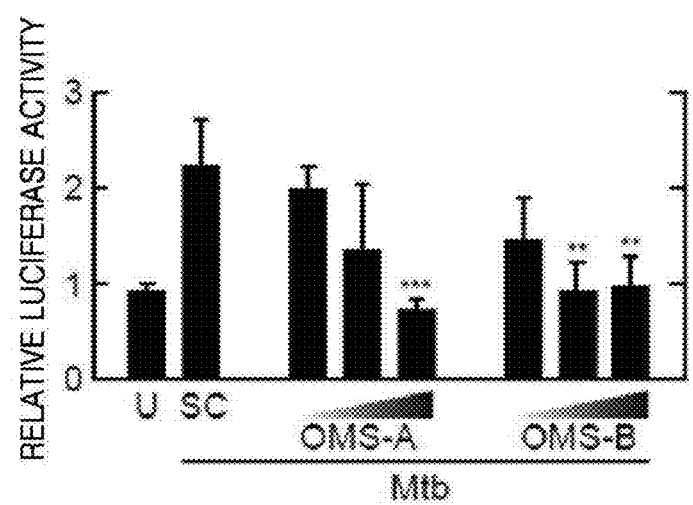
FIG. 12B is a graph of an expression level of NF-κB in Mtb-infected macrophages treated with OMS-A or OMS-B.

In addition, a macrophage was transfected with a vector including nuclear factor kappa-light-chain-enhancer of activated B cell (NF-κB)-luciferase reporter gene (available from Genetransfer Vector Core), followed by infection with Mtb. Subsequently, 1 µM, 5 µM, or 10 µM of OMS-A and OMS-B were added thereto, followed by incubation for about 6 hours. Subsequently, cell lysate was obtained from the macrophage, and luciferase activity of cell lysate was measured. The measured luciferase activity is shown in FIG. 12B ("U" represents "untreated", "SC" represents" "solvent control", *: p<0.001, and : p<0.01). As shown in FIG. 12B, in the case of treatment of a Mtb-infected macrophage with OMS-A or OMS-B, luciferase activity decreases in a concentration-dependent manner, thereby inhibiting expression of NF-κB, which is an inflammation inducing factor.

Therefore, it was found that OMS-A and OMS-B alleviate inflammatory response of the Mtb-infected macrophage.

As apparent from the foregoing description, the compound including a peptide of Formula 1, or an isomer, a derivative, a solvate, or a pharmaceutically acceptable salt thereof has anti-*Mycobacterium tuberculosis* activity against Mycobacteria, e.g., *Mycobacterium tuberculosis*, and alleviate inflammatory response caused by *Mycobacterium tuberculosis*. Thus, the compound including a peptide of Formula 1, or an isomer, a derivative, a solvate, or a pharmaceutically acceptable salt thereof may be used in preventing or treating *Mycobacterium* sp. infection or a related symptom thereof.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the disclosure as defined by the following claims.

What is claimed is:

1. A method of treating *Mycobacterium* sp. infection or a related symptom thereof, the method comprising administering a pharmaceutical composition into a subject,
   wherein the pharmaceutical composition comprises:
   a compound comprising a peptide represented by Formula 3 or Formula 4, or a stereoisomer, a derivative, a solvate, or a pharmaceutically acceptable salt thereof:

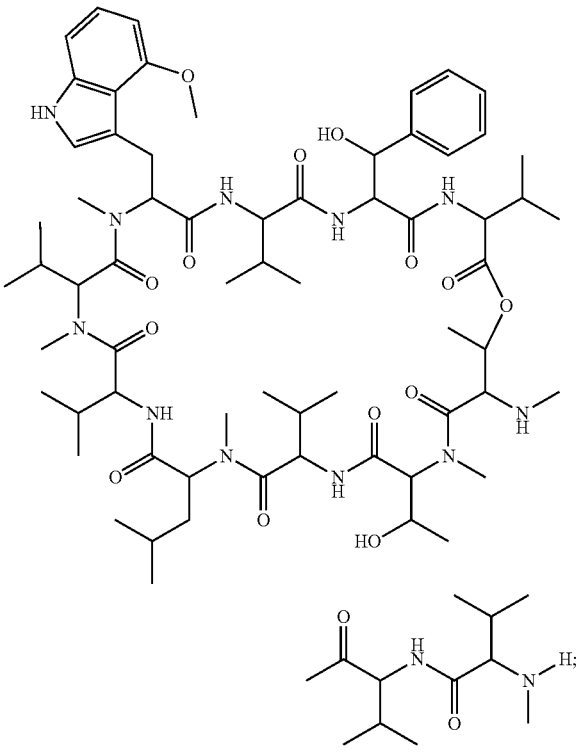

Formula 3 and

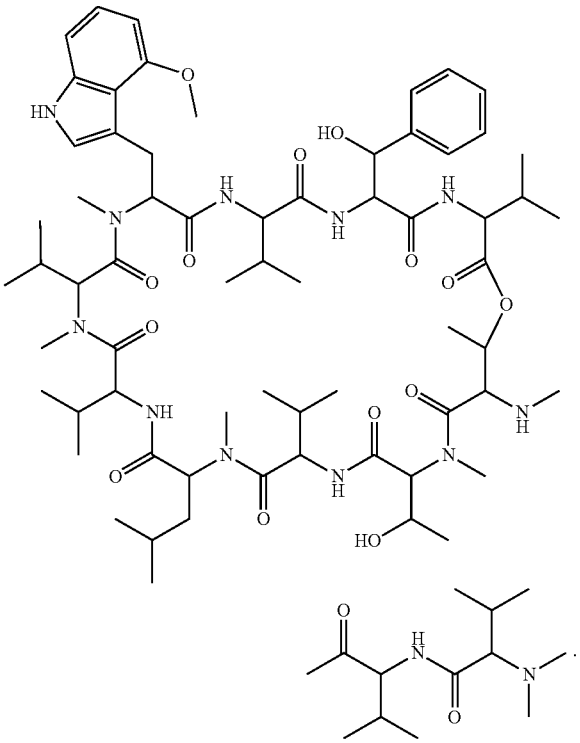

Formula 4

2. The method of claim 1, wherein the *Mycobacterium* sp. infection is selected from tuberculosis, leprosy, and nontuberculous mycobacteria (NTM) infection.

3. The method of claim 2, wherein tuberculosis is multidrug-resistant (MDR) tuberculosis or extensively drug-resistant (XDR) tuberculosis.

4. The method of claim 1, wherein the related symptom is inflammation.

5. The method of claim 1, wherein the *Mycobacterium* sp. infection is caused by *Mycobacterium tuberculosis*.

6. The method of claim 1, wherein the compound comprising the peptide represented by Formula 3 or Formula 4. or an isomer a stereoisomer, a derivative, a solvate, or a pharmaceutically acceptable salt thereof promotes autophagy of macrophage, alleviates inflammation, or induces a combination thereof.

7. The method of claim 1, further comprising administering antibiotics to the subject.

8. The method of claim 7, wherein the antibiotics is antituberculosis drug.

9. The method of claim 8, wherein the antituberculosis drug is isoniazid, rifampicin, ethambutol, SQ-109, pyrazinamide, streptomycin, kanamycin, capreomycin, ethionamide, prothionarnide, enviomycin, para-arninosalicylic acid, cycloserine, amikacin, levofloxacin, moxifloxacin, gatifloxacin, ofloxacin, terizidone, thionamide, ethionamide, protionamide, clofazimine, linezolid, amoxicillin, clavulanate, thioacetazone, imipenem, cilastatin, clarithromycin, bedaquiline, delamanid, Imipenem, cilastatin, meropenem, or a combination thereof.

* * * * *